United States Patent
Hatlestad (10) Patent No.: US 7,471,986 B2
(45) Date of Patent: Dec. 30, 2008

(54) SYSTEM AND METHOD FOR TRANSMITTING ENERGY TO AND ESTABLISHING A COMMUNICATIONS NETWORK WITH ONE OR MORE IMPLANTED DEVICES

(75) Inventor: John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 376 days.

(21) Appl. No.: 10/783,285

(22) Filed: Feb. 20, 2004

(65) Prior Publication Data

US 2005/0187594 A1  Aug. 25, 2005

(51) Int. Cl.
*A61N 1/00* (2006.01)
*A61N 1/08* (2006.01)

(52) U.S. Cl. .............. 607/61; 607/60; 607/30; 607/32; 607/33; 607/34

(58) Field of Classification Search ............. 607/60–61, 607/30, 32–34
See application file for complete search history.

(56) References Cited

U.S. PATENT DOCUMENTS

| | | | | |
|---|---|---|---|---|
| 4,082,097 A | * | 4/1978 | Mann et al. | 607/33 |
| 5,519,262 A | | 5/1996 | Wood | |
| 5,630,836 A | * | 5/1997 | Prem et al. | 607/61 |
| 5,741,314 A | * | 4/1998 | Daly et al. | 607/60 |
| 5,749,909 A | * | 5/1998 | Schroeppel et al. | 607/33 |
| 5,876,425 A | * | 3/1999 | Gord et al. | 607/56 |
| 6,006,132 A | | 12/1999 | Tacker, Jr. et al. | |
| 6,047,214 A | * | 4/2000 | Mueller et al. | 607/61 |
| 6,083,174 A | | 7/2000 | Brehmeier-Flick et al. | |
| 6,140,740 A | | 10/2000 | Porat et al. | |
| 6,198,965 B1 | | 3/2001 | Penner et al. | |
| 6,212,430 B1 | * | 4/2001 | Kung | 607/61 |
| 6,239,724 B1 | | 5/2001 | Doron et al. | |
| 6,240,318 B1 | | 5/2001 | Phillips | |
| 6,249,703 B1 | | 6/2001 | Stanton et al. | |

(Continued)

OTHER PUBLICATIONS

Benedetti, R. et al., "Overview of Telemetry Systems with Inductive Links and Variable Coupling Distances," *Biotelemetry XIII*, pp. 57-62, Williamsburg Lodge, Williamsburgh, Virginia, (Mar. 26-31, 1995).

*Primary Examiner*—Carl H Layno
*Assistant Examiner*—Natasha N Patel
(74) *Attorney, Agent, or Firm*—Schewgman, Lundberg & Woessner, P.A.

(57) ABSTRACT

Systems and methods for automatically powering and communicating with an implantable medical device through an inductive link are disclosed. A preferred embodiment comprises an inductive coil or set of such coils. One coil may be mounted or installed on or near the bed of a patient as a component of a transmission module. Another coil may a component of an implantable medical device. The coils are energized by a resonant circuit to generate an electromagnetic field in the vicinity of the bedside. Without any action on the patient's part, the implantable device receives the inductively transmitted energy to power its immediate operation or recharge its battery, thereby extending its longevity, potentially indefinitely. The inductive link also enables data transfer communication between the transmission module and implantable device. Some embodiments of a system disclosed herein also can be configured as a component of an Advanced Patient Management System that helps better monitor, predict and manage chronic diseases.

51 Claims, 5 Drawing Sheets

U.S. PATENT DOCUMENTS

| | | |
|---|---|---|
| 6,277,078 B1 | 8/2001 | Porat et al. |
| 6,345,203 B1 | 2/2002 | Mueller et al. |
| 6,358,281 B1 | 3/2002 | Berrang et al. |
| 6,381,496 B1 | 4/2002 | Meadows et al. |
| 6,431,175 B1 | 8/2002 | Penner et al. |
| 6,432,050 B1 | 8/2002 | Porat et al. |
| 6,442,434 B1 * | 8/2002 | Zarinetchi et al. ............. 607/61 |
| 6,475,170 B1 | 11/2002 | Doron et al. |
| 6,486,588 B2 | 11/2002 | Doron et al. |
| 6,504,286 B1 | 1/2003 | Porat et al. |
| 6,628,989 B1 | 9/2003 | Penner et al. |
| 6,720,709 B2 | 4/2004 | Porat et al. |
| 6,764,446 B2 | 7/2004 | Wolinsky et al. |
| 6,840,956 B1 | 1/2005 | Wolinsky et al. |
| 6,855,115 B2 | 2/2005 | Fonseca et al. |
| 7,024,248 B2 | 4/2006 | Penner et al. |
| 7,147,604 B1 | 12/2006 | Allen et al. |
| 7,198,603 B2 | 4/2007 | Penner et al. |
| 7,245,117 B1 | 7/2007 | Joy et al. |
| 7,273,457 B2 | 9/2007 | Penner |
| 7,283,874 B2 | 10/2007 | Penner |
| 2001/0026111 A1 | 10/2001 | Doron et al. |
| 2001/0041920 A1 | 11/2001 | Starkweather et al. |
| 2002/0045921 A1 | 4/2002 | Wolinsky et al. |
| 2002/0065540 A1 * | 5/2002 | Lebel et al. .................... 607/60 |
| 2002/0072785 A1 | 6/2002 | Nelson et al. |
| 2002/0077673 A1 | 6/2002 | Penner et al. |
| 2002/0082665 A1 | 6/2002 | Haller et al. |
| 2002/0173830 A1 | 11/2002 | Starkweather et al. |
| 2002/0177782 A1 | 11/2002 | Penner et al. |
| 2003/0014090 A1 * | 1/2003 | Abrahamson ................ 607/60 |
| 2003/0083698 A1 * | 5/2003 | Whitehurst et al. ............ 607/3 |
| 2004/0172083 A1 | 9/2004 | Penner |
| 2004/0204744 A1 | 10/2004 | Penner et al. |
| 2004/0225337 A1 * | 11/2004 | Housworth et al. ........... 607/60 |
| 2005/0043605 A1 * | 2/2005 | Hall et al. ................... 600/382 |
| 2006/0196277 A1 | 9/2006 | Allen et al. |
| 2006/0283007 A1 | 12/2006 | Cros et al. |
| 2006/0287602 A1 | 12/2006 | O'Brien et al. |
| 2006/0287700 A1 | 12/2006 | White et al. |
| 2007/0096715 A1 | 5/2007 | Joy et al. |
| 2007/0100215 A1 | 5/2007 | Powers et al. |
| 2007/0199385 A1 | 8/2007 | O'Brien |
| 2007/0210786 A1 | 9/2007 | Allen et al. |
| 2007/0274565 A1 | 11/2007 | Penner |
| 2008/0015421 A1 | 1/2008 | Penner |
| 2008/0077440 A1 | 3/2008 | Doron |
| 2008/0103553 A1 | 5/2008 | Penner et al. |
| 2008/0108915 A1 | 5/2008 | Penner |

* cited by examiner

SYSTEM AND METHOD FOR TRANSMITTING ENERGY TO AND ESTABLISHING A COMMUNICATIONS NETWORK WITH ONE OR MORE IMPLANTED DEVICES

TECHNICAL FIELD

The present device relates generally to implantable medical devices and particularly, but not by way of limitation, to an external device that can provide energy to and communicate with the implantable device or a network of such devices through inductive and/or telemetric coupling.

BACKGROUND

Implantable devices are indicated for an increasing number of patients and an increasing variety of medical conditions. Fully implantable systems are preferred to avoid the need to carry and maintain an external power source, which is inconvenient to the patient and serves as a constant source of worry because the patient is continuously aware of the device. However, fully implantable systems often place design constraints on the power consumption of the device due to the competing objectives of high device longevity versus device compactness.

The use of inductive power coupling of implantable medical devices to help solve this power/size dichotomy is well known. For example, inductive power coupling has been utilized in LVAD (artificial hearts), cochlear implants and respiratory pacemakers.

Inductive power links are of two main types—tightly coupled links versus loosely coupled links. Tightly coupled links are typically characterized by known or close distances between the transmission and reception components. In addition, the geometry of tightly coupled links is typically known or fixed. In contrast, loosely coupled systems operate over variable distances and with unknown or variable geometric orientations. However, loosely coupled systems are typically characterized by low power transmission efficiencies.

Systems to transmit power across a variable coupling distance of 4-8 cm have been demonstrated to attain a transmission efficiency of about 10%. See Benedetti, R. et al., *Overview of Telemetry Systems With Inductive Links and Variable Coupling Distances*, International Conference on Biotelemetry XIII, March 1995, which is incorporated herein by reference. Systems of this nature have been implemented with transmitter output power from about 100 mW to about 15 Watts. Even if a practical system is limited to 1% efficiency, the amount of power transferable to the implanted device while coupled to the power transmitter can be substantial (relative to the power budget of the typical implanted device). Such inductive power coupling links also have been designed to accommodate two-way or bi-directional communication between the implant and the external device.

Because of the energy/power transfer and communications link capabilities of inductive coupling, it can be used to provide power to multiple devices simultaneously, provide communications with multiple devices simultaneously and provide communications between multiple implantable devices.

A basic example of inductive coupling can be found in U.S. Pat. No. 5,519,262 to Wood. The '262 patent discloses a system for power coupling independent of the position of the receiver over a surface by using a spatially-dependent phase shift in the electromagnetic field generated by the power transmitter. In addition, the '262 patent generally discloses, without specific examples, the potential use of the invention in power and communications transmission. However, the '262 patent does not disclose or claim the use of the technology to power or access data from an implantable medical device.

U.S. Pat. No. 6,083,174 to Brehmeier-Flick et al. discloses an implantable sensor and two telemetry units—one implanted with the sensor within a flexible foil and the other extracorporeal. Although the '174 patent discloses the implanted telemetry unit as being adapted to receive a conductive power transmission from the extracorporeal telemetry unit and to transmit data to that unit, the patent explicitly disclaims the need for an implanted battery. Therefore, the invention described in the '174 patent is incapable of recharging an energy storage device implanted with the medical device. In addition, although the '174 patent describes the use of a personal computer to capture and analyze sensed patient data, it does not disclose the use of a computer network to analyze and correlate sensed patient data from a population of patients.

U.S. Pat. No. 6,240,318 to Phillips discloses a transcutaneous energy transmission system (TETS) to provide power for any kind of implantable device requiring a source of DC power operation. The implantable device may be a mechanical circulatory support system, a left ventricular device, a muscle stimulator, vision prosthesis, audio prosthesis or other implantable device requiring DC electrical power operation. The TETS system is also adapted to recharge an implantable battery. However, the '318 patent is limited to powering devices and is not adapted to communicate patient data to external diagnostic or analytical devices.

U.S. Pat. No. 6,345,203 to Mueller, et al. discloses the use of Magnetic Vector Steering and Half-Cycle Amplitude Modulation to enhance the powering and control of multiple, arbitrarily oriented implant devices. These techniques, according to the patent, enable arbitrarily oriented implants to receive power and command, programming, and control information in a manner that preserves battery life and transmission time while reducing overall implant device bulk. More specifically, the invention of '203 patent is suitable for high-bandwidth (>1 Mbits/sec) biotelemetry that requires large amounts of energy to power the implant. Consequently, the patent suggests alternative or supplemental power sources, such as Inductive Power Transfer. In addition, the preferred use of the invention of the '203 patent is in biomedical implants placed in regions of interest about the heart of a patient. However, the '203 patent does not disclose or claim the use of induction technology to automatically recharge the battery of an implantable medical device and provide intercommunications capability with the device in proximity to an electromagnetic transmission source.

In contrast, U.S. Pat. No. 6,358,281 to Berrang, et al. discloses a cochlear device, which can be implanted, that uses an external, mechanically held, head-mounted device containing an external coil inductively coupled to a receiving coil to periodically recharge the implanted battery of the device. The external and implanted coils also can be used as a communications link to program the implanted electronics of the device. However, the device disclosed in the '281 patent is limited to a cochlear prosthesis and is not for use beyond this limited application. In addition, the inductive coil of the implant is only configured "for receiving" data from an external means. The patent does not disclose uploading data from the implant to an analytical device or network.

Thus, for these and other reasons, there is a need for an automatic system that inductively transmits energy to an implantable medical device to power or recharge the battery of the device and fully communicate with the device or a network of such devices to improve individual patient care or the care of populations of patients. The system further eliminates the need to attach or carry an external device to enable power transmission and intercommunication.

SUMMARY

According to one aspect of the invention, there is provided a system and method for automatically powering and communicating with an implantable medical device through an inductive transfer link, thereby providing means to periodically provide energy to the implantable medical device (or devices) to either power its immediate operation or to recharge an energy storage device (e.g., a battery) contained in the implant. In addition to the transmission of power, a transfer link can be established to enable data communication with the device or a network comprising multiple devices. For example, the inductive link may power intracorporeal ultrasound transmitters and receivers for data communication between multiple implantable devices. In either powering or communications modes, the transfer link is controlled or regulated. As used herein, a "clinician" can be a physician, physician assistant (PA), nurse, medical technologist, or any other patient health care provider.

Without any action on the patient's part, the implantable device receives the transmitted energy to power its immediate operation or recharge its battery. In addition to energy transfer, a bedside inductive system may mediate data communications through modulation on the inductive link itself or through independent (i.e., RF) means. In this way, the implantable medical device may communicate with an analytical device or programmer to automatically monitor or upload biometric data, or program the device without discharging the battery while performing those tasks. In this embodiment, the implantable medical device is adapted to electronically store biometric data.

In another embodiment, the system may be a component of a larger network of implantable devices that allow centralized or nodal monitoring of the health status or condition of a population of patients. Inter-device communication or data transfer between implanted devices may be mediated through the inductively coupled external device or directly with another device.

The disclosure herein may apply to any type of implantable device whose operation may be limited by constrained power resources. In a preferred embodiment, the system includes a transmission module comprising at least one energizable coil mounted near a patient's bed, either in a bedside monitoring device (for example the Advanced Patient Management ("APM") bedside repeater) or, if necessary to get sufficient power coupling, under the patient's mattress or mattress pad. As known to those of skill in the art, a repeater comprises a system and device that electronically collects information from an implantable medical device and transmits that information to a centralized computer network or server for analysis. This embodiment also contemplates a complementary implantable medical device comprising at least one energizable coil to inductively link or couple with the transmission module. The system as described herein potentially removes or greatly relaxes a significant constraint in the design of implantable devices—that of power consumption.

The various embodiments described above are provided by way of illustration only and should not be construed to limit the invention. Those skilled in the art will readily recognize various modifications and changes that may be made to the present system without following the example embodiments and applications illustrated and described herein, and without departing from the true spirit and scope of the present system, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which are shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The disclosure herein may apply to any type of implantable device whose operation may be limited by constrained power resources. This disclosure certainly applies to traditional cardiac rhythm management devices, but also to other types of implantable devices. It may enable development of extremely small, minimally invasive implantable (potentially injectable) sensing devices distributed throughout the human body, which could communicate wirelessly with one another and/or with a traditional cardiac rhythm management device to provide more complete diagnostic or analytical capabilities. For example, Muscle Sympathetic Nerve Activity (MSNA) may be measured with an injectable, microelectrode-sensing device.

After a simple initial setup procedure, the system is fully automatic for the patient. The system comprises a coil or set of coils to be mounted or installed on or near the bed of the patient. These coils are energized by a resonant circuit to generate an electromagnetic field in the vicinity of the bedside. The implanted device includes a complementary receiving coil circuit tuned to the same frequency as the transmitting coil(s), and a circuit to convert and store the received energy (e.g., a rectifying circuit). Without any action on the patient's part, the implantable device receives the transmitted energy to power its immediate operation or to recharge its energy storage device, thereby extending its longevity, potentially indefinitely.

Since there are few, if any practical constraints on the amount of power available to the transmitter (it could be plugged into a wall socket), the only practical limitations on the radiated power may be those related to patient safety and electromagnetic compatibility. Thus, in the absence of concern about prolonged exposure to the electromagnetic field, the relatively low achievable transmission energy efficiency may not be of great concern.

The system as described herein potentially removes or greatly relaxes a significant constraint in the design of implantable devices—that of power consumption. With this relaxed constraint, designers would have added freedom to:
- Increase the longevity of implanted devices;
- Reduce the size of implanted devices;
- Increase the power budget of implanted devices to enable;
  - Increased processing power;
  - Increased data storage;
  - Increased sensing abilities; and
  - Increased therapy abilities;
- Communicate with implanted sensors distributed throughout the body to enable;
  - Improved diagnostic abilities, especially in an APM environment;
  - Improved therapeutic abilities; or
  - Any combination of the above.

Figure 1:
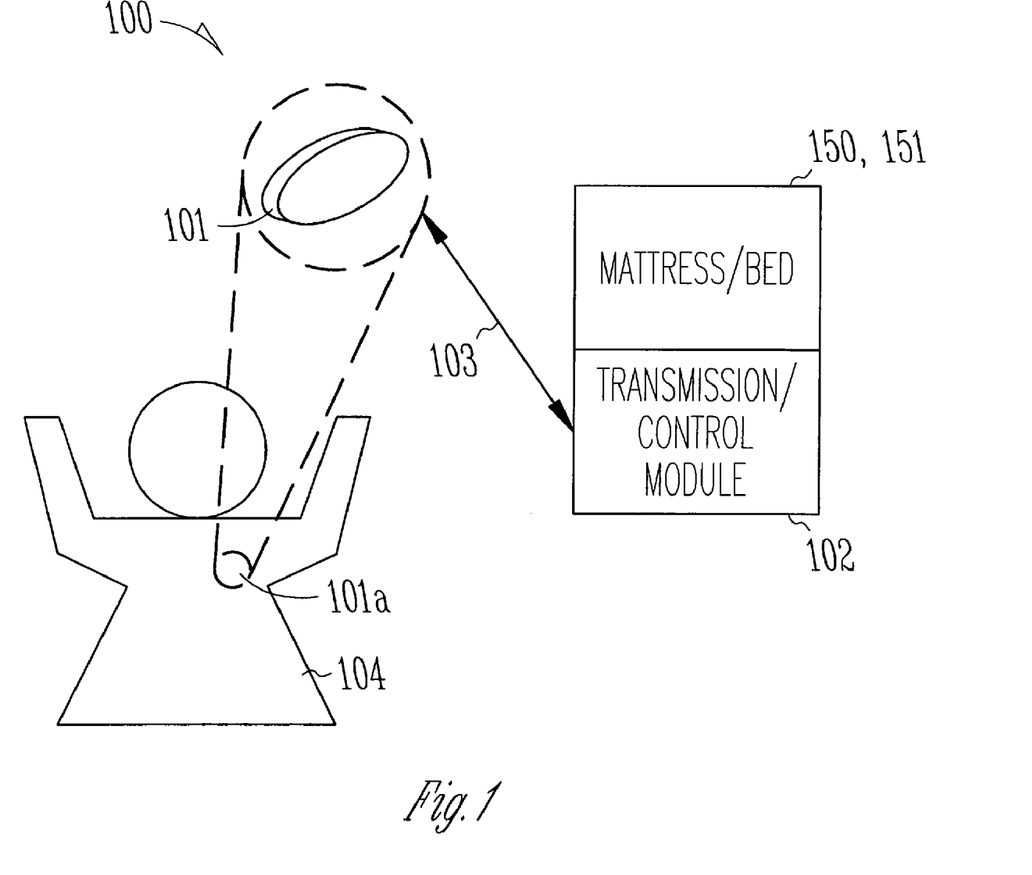
FIG. 1 is a schematic/block diagram illustrating generally, among other things, a system for automatically establishing a powering and communications link with an implantable medical device using an inductive and/or telemetric couple.

FIG. 1 is a schematic/block diagram illustrating generally, among other things, a system 100 for automatically establishing a powering and communications link with an implantable medical device 101, said system comprising a transmission module 102 for establishing and controlling an inductively coupled link 103 adapted to power and communicate with an implantable medical device 101. Such a medical device 101, 101a may include a traditional cardiac rhythm management device ("CRM"), like a pacemaker or implantable defibrillator, but may also include other implantable devices adapted to monitor and sense other biometric parameters such as electroencephalograph ("EEG") impulses, electromyography or electrical muscle measurement ("EMG"), MSNA, thoracic pressure, hemodynamic pressure other nerve conduction parameters, and various sleep parameters and positions. For example, traditional sleep clinic sensors for measuring EEG, EMG, and electrooculograph ("EOG") may need to operate only while a patient 104 is lying in bed, which is when the power source described herein could be available to the patient 104.

Figure 2:
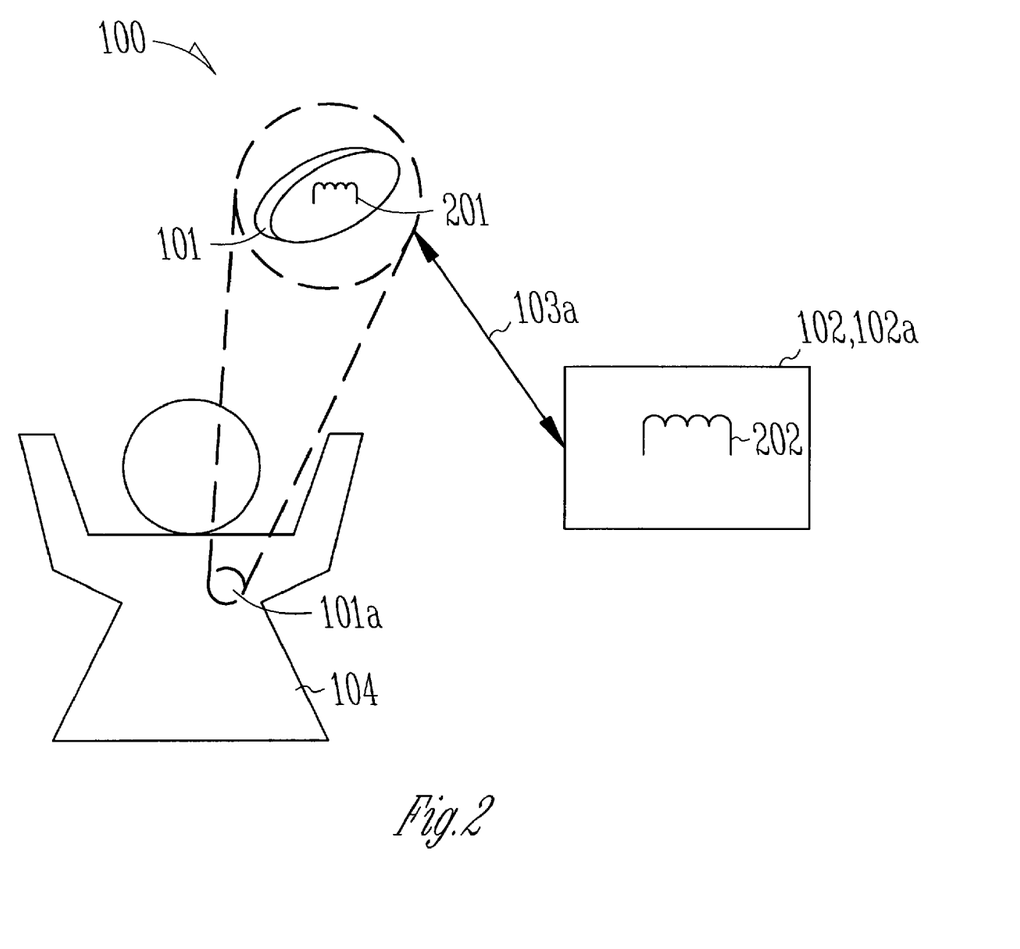
FIG. 2 is a schematic/block diagram illustrating generally, among other things, an embodiment of the coils of the system to electromagnetically couple and link an extracorporeal device with an implantable medical device.

As shown in FIG. 2, the disclosure herein contemplates that energizable coils 201, 202 are mounted near the patient's 104 bed 150, either in transmission module 102 comprising a bedside monitor device 102a (for example the APM bedside repeater) or, if necessary to get sufficient power coupling, under the patient's 104 mattress 151 or mattress pad. In this configuration, the system 100 comprises a loosely coupled inductive power link 103a. When the patient 104 lies in bed, the coils in the implanted device(s) receive the radiated power and use it to power the device's 101, 101a immediate and/or continuing operation. Preferably, the system automatically establishes the inductive link 103a whenever the patient 104 is in or near a bed adapted with energizable coils, or at night while the patient 104 is in or near such a bed.

FIG. 2 also illustrates a method of using a system 100 to establish an inductive link an implantable medical device 101a and a transmission module 102. The method comprises the steps of bringing the implantable medical device 101 may within operational proximity to the transmission module 102 to automatically establish a loosely coupled inductive link 103a between the device 101a and the module 102. Once established, the inductive link is regulated to transfer power from the transmission module 102 to the implantable medical device 101a and/or transfer data between the module 102 and the implantable medical device 101a. The method may further comprise the step of recharging an energy storage device of the implantable medical device 101a.

Figure 3:
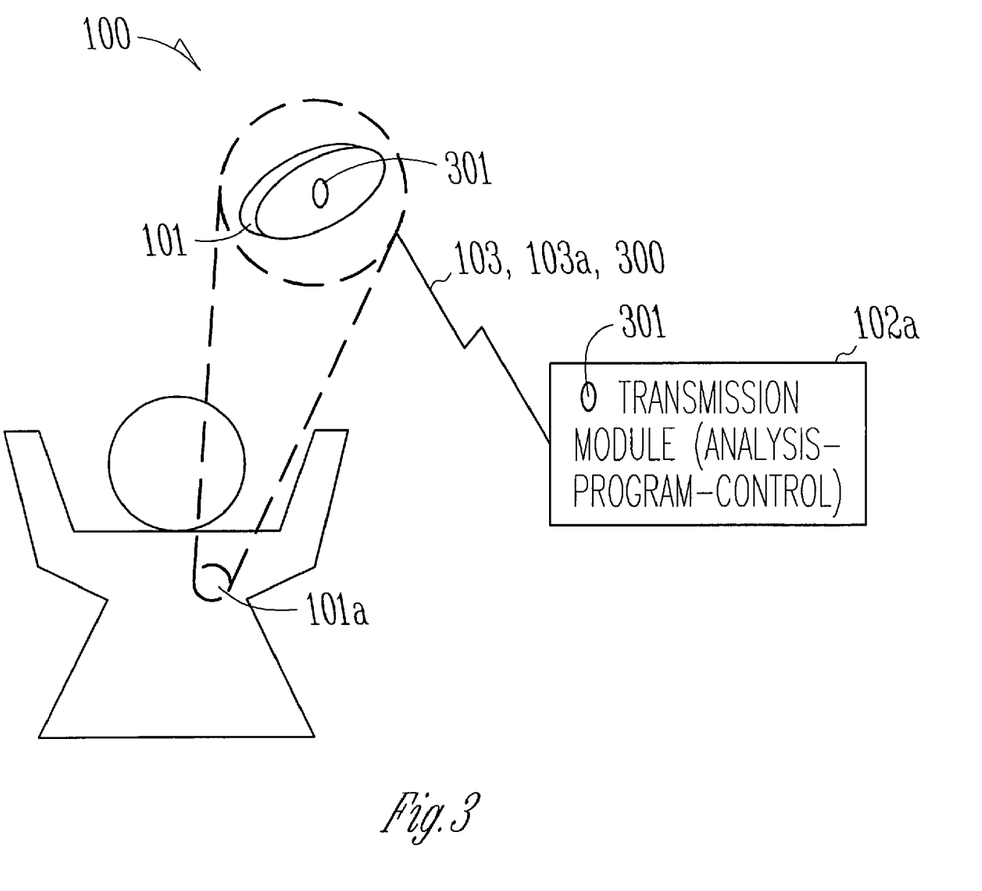
FIG. 3 is a schematic/block diagram illustrating generally, among other things, another embodiment of a system with an implantable medical device in communication with an extracorporeal analytical device or programmer to automatically monitor or upload biometric data or program the device without discharging the battery.

In addition to energy transfer, a bedside inductive system may mediate communications through modulation of the inductive link itself or through independent (i.e., RF) means. Communication may be bi-directional to allow upload and download of data. As shown in FIG. 3, the inductive system 100 is adapted to allow an implantable medical device 101, 101a to communicate 300 with a transmission module that may be further adapted to comprise an analytical device or programmer 102a to automatically monitor, download or upload biometric data and/or program the implantable device 101, 101a without discharging the device's battery in addition to controlling the link 103, 103a, 300 between the transmission module 102a and the implantable medical device 101, 101a. The independent communications means may include a Bluetooth® RF transmitter and receiver 301 as a component of the device 101 and programmer 102a that derives power from the inductive link 103, 103a.

Figure 4:
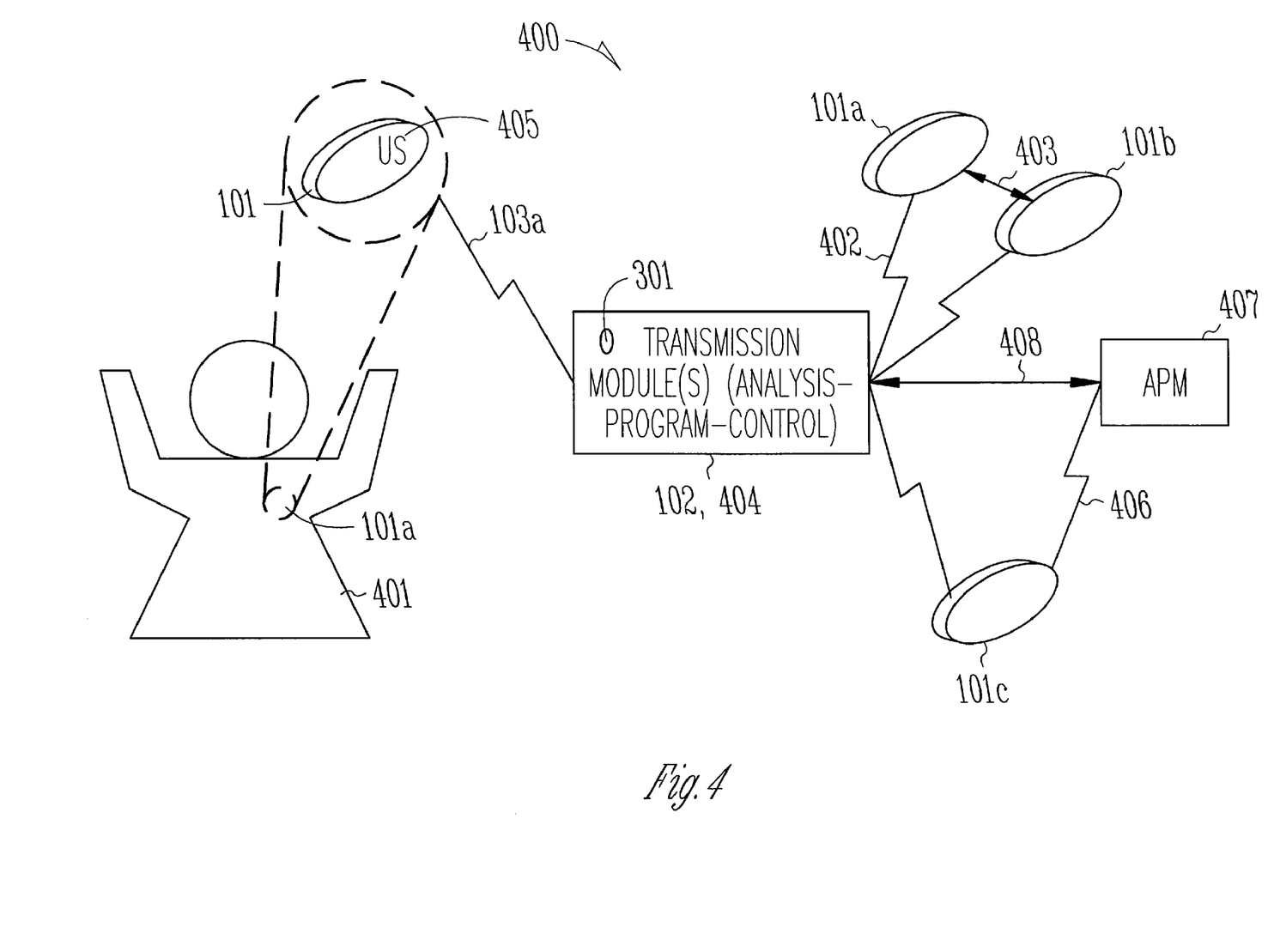
FIG. 4 is a schematic/block diagram illustrating generally, among other things, the system as a component of a larger network of implantable devices.

The system may also be a component of a larger network 400 of implantable devices that allow centralized or nodal monitoring of the health status or condition of a population of patients 401. FIG. 4 illustrates an embodiment adapted to communicate 402 with multiple implantable devices 101a, 101b, 101c and other medical devices that may be implanted within the same patient or other patients and that may be enabled and/or mediated through an inductive link 103a. Inter-device communication 403 between implanted devices may be mediated through an inductively coupled external device 102, 404 or direct device-to-device communication may be enabled by the additional power/energy available to the implanted device through the inductive power coupling of the internal and external devices. The inductive link may be further adapted to power intra-corporeal ultrasound transmitters and receivers 405 for communication between multiple, implantable devices. Intercommunication 403 between multiple implantable sensor/therapy modules or devices 101a, 101b, 101c mediated through transmission modules 102, 404 may be further adapted to electronically communicate on a network to share data 406 with another external device like an APM system 407 accessible by the patient and/or a clinician. APM provides more accurate real-time adaptive therapy based on more comprehensive information about the status of a patient.

As further shown in FIG. 4, a method of using the system may include establishing an inductive link 103a to power data transfer 402 between a plurality of implantable medical devices 101a, 101b and 10c. It is further contemplated the method includes the step of the transmission module 404 analyzing the data 402 transferred from implantable medical devices 101a, 101b, 101c, said data comprising biometric parameters. The method may also include the step of powering data transfer 406 between an implantable medical device 101c and an APM system 407. Such communication 406 can be mediated directly with the APM 407 or through an electronic connection 408 with transmission module 404.

Figure 5:
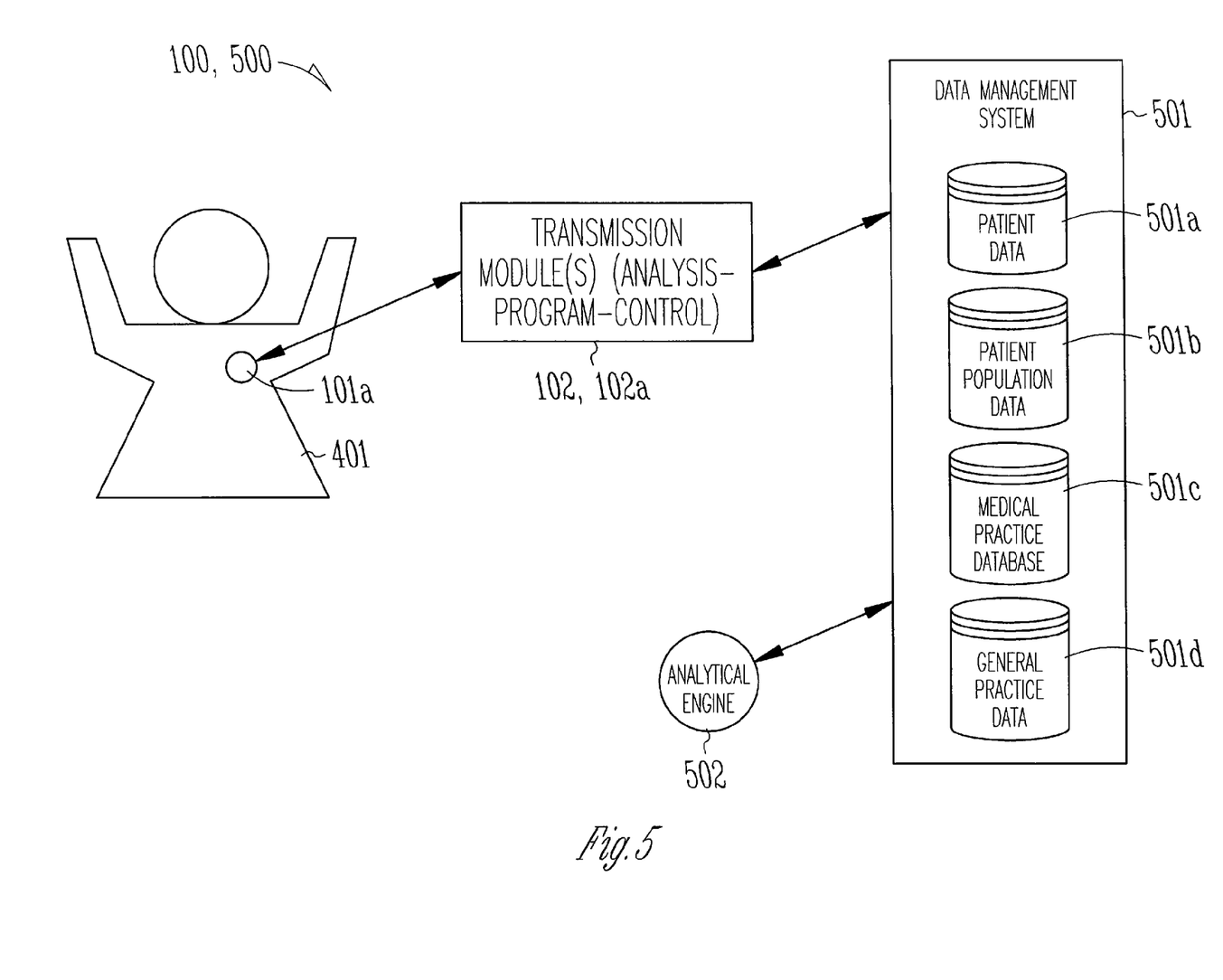
FIG. 5 is a schematic/block diagram illustrating generally, among other things, an embodiment of the system as a component of an Advanced Patient Management system.

FIG. 5 illustrates generally, among other things, an embodiment comprising an APM that not only provides the system 100, 500 with power advantages, but also is adapted to communicate with a larger network of implantable devices with APM capabilities to allow the clinician to monitor and control a population of patients 401. APM is a system that helps patients, their physicians and their families to better monitor, predict and manage chronic diseases. APM is particularly useful in maintaining long-term data continuity and combining information from medical devices, including the system for powering and communicating with an implantable medical device 101*a* disclosed herein, with patient data from other medical databases. In the embodiment shown in FIG. 5, the APM system 500 comprises three primary components: 1) a transmission module, 102, 102*a;* 2) an implantable medical device 101*a*, including at least one sensor adapted to monitor physiological functions; 3) a data management system 501 comprising patient 501*a*, 501*b* and medical 501*c*, 501*d* databases; and 4) an analytical engine 502 that analyzes data from the data management module. APM is designed to support physicians and other clinicians in using a variety of different devices, patient-specific and non-specific data, along with medication therapy, to provide the best possible care to patients.

The various embodiments described above are provided by way of illustration only and should not be construed to limit the invention. The above-described embodiments may be used in combination with each other. Those skilled in the art will readily recognize various modifications and changes that may be made to the present invention without following the example embodiments and applications illustrated and described herein, and without departing from the true spirit and scope of the present invention, which is set forth in the following claims and their equivalents. In the appended claims, the terms "including" and "in which" are used as the plain-English equivalents of the respective terms "comprising" and "wherein."

What is claimed is:

1. A system for transmitting energy to and communicating with a complementary implantable medical device, the system comprising a transmission module further comprising at least one energizable coil and adapted to automatically establish and control an inductive transfer link with the complementary implantable medical device comprising at least one energizable coil wherein the transmission module automatically initiates, without requiring user intervention, patient contact, or any alignment between the energizable coil and the implantable medical device, an inductive transfer of energy to the medical device to power the medical device, the automatic initiation based at least in part on the medical device coming within range of the transmission module, wherein the transmission module establishes a data transfer link with the medical device and wherein the inductive link powers the data link and wherein the inductive link powers at least one of: (1) intracorporeal ultrasound transmitters and receivers for data communication between multiple implantable devices, or (2) a RF transmitter and receiver.

2. The system of claim 1, wherein the transmission module automatically establishes and controls the inductive link when the complementary implantable medical device is adjacent the transmission module.

3. The system of claim 1, wherein the transmission module automatically establishes and controls the inductive link when the complementary implantable medical device is adjacent the transmission module at night.

4. The system of claim 1, wherein the at least one coil of the transmission module is adjacent a patient's bed such that the transmission module automatically establishes and controls the inductive link with the implantable medical device when the patient is in the patient's bed.

5. The transmission module of claim 4, wherein the transmission module automatically establishes and controls the inductive link when the complementary implantable medical device is adjacent the bed at night and the patient is in the bed.

6. The transmission module of claim 1, wherein the at least one coil of the transmission module is configured to communicate with the at least one coil of the complementary implantable medical device at a location that is adjacent a patient's mattress.

7. The system of claim 6, wherein the transmission module automatically establishes and controls the inductive link when the complementary implantable medical device is adjacent the mattress.

8. The system of claim 6, wherein the transmission module automatically establishes and controls the inductive link when the patient with a complementary implantable medical device is adjacent the mattress at night.

9. The system of claim 1, wherein the device includes a cardiac rhythm management device.

10. The system of claim 1, wherein the device comprises sensors that include at least two of EEG, EMG, EOG, MSNA, thoracic pressure, and hemodynamic pressure sensors.

11. The system of claim 10, wherein the sensors include sensors adapted to replicate the sensing of a sleep clinic study.

12. The system of claim 1, wherein the link includes a loosely coupled inductive link.

13. The system of claim 12, wherein the link is established when the transmission module is about 10 centimeters from the medical device.

14. The system of claim 12, wherein the link is established when the transmission module is less than 10 centimeters from the medical device.

15. The system of claim 14, wherein the link is established when the transmission module is about 4-8 centimeters from the medical device.

16. The system of claim 12, wherein the link is established when the transmission module is more than 10 centimeters from the medical device.

17. The system of claim 1, wherein the transmission module transfers energy to the medical device to power the device.

18. The system of claim 1, wherein the transmission module transfers energy to the implantable medical device to recharge a battery of the implantable medical device.

19. The system of claim 1, wherein the data link is a bi-directional data transfer link that is adapted to upload and download data.

20. The system of claim 1, wherein the transmission module establishes a data transfer link with a plurality of medical devices.

21. The system of claim 1, wherein the transmission module establishes a data transfer link with a centralized patient management system.

22. The system of claim 1, wherein the inductive link modulates the data link.

23. The system of claim 1, wherein the inductive link powers intracorporeal ultrasound transmitters and receivers for data communication between multiple implantable devices.

24. The system of claim 1, wherein the inductive link powers a RF transmitter and receiver.

25. The system of claim 24, wherein the RF transmitter and receiver comprises a Bluetooth® RF transmitter and receiver.

26. The system of claim 24, wherein the transmission module comprises a RF transmitter and receiver.

27. The system of claim 24, wherein the implantable medical device comprises a RF transmitter and receiver.

28. The system of claim 24, wherein the transmission module and the implantable medical device comprise an RF transmitter and receiver.

29. A system for transmitting energy to and communicating with an implantable medical device, the system comprising a transmission module adapted to automatically establish and control an inductive transfer link with the implantable medical device, said module comprising at least one energizable coil, and said implantable medical device comprising at least one energizable coil, an energy storage device and memory to electronically store data, and wherein the transmission module is further adapted with memory to electronically store data.

30. The system of claim 29, wherein the transmission module transfers power to the implantable medical device and recharges the energy storage device.

31. The system of claim 29, wherein the transmission module establishes a data link with the implantable medical device.

32. The system of claim 29, wherein the transmission module establishes a data link with a plurality of implantable medical devices.

33. The system of claim 29, wherein the transmission module establishes a data link with a centralized patient management system.

34. The system of claim 29, wherein the transmission module establishes a bi-directional data link with the implantable medical device.

35. The system of claim 29, wherein the transmission module is further adapted to analyze data comprising biometric parameters.

36. A method of using the system for transmitting energy to and communicating with an implantable medical device, the system comprising a transmission module adapted to automatically establish and control an inductive transfer link with a complementary implantable medical device, said module comprising at least one energizable coil, and said medical device comprising at least one energizable coil, an energy storage device and memory to electronically store data, wherein the method comprises the steps of
  a. bringing the implantable medical device within operational proximity to the transmission module;
  b. automatically establishing an inductive transfer link between the implantable medical device and the transmission module;
  c. regulating the inductive link;
  d. transferring power to the implantable medical device;
  e. transferring data to and from the implantable medical device; and
  f. powering communication between the implantable medical device and a centralized patient management system.

37. The method of claim 36, wherein the method further comprises the step of recharging the energy storage device of the implantable medical device.

38. The method of claim 36, wherein the method further comprises the step of powering data transfer between a plurality of implantable medical devices.

39. The method of claim 36, wherein the method further comprises the step of analyzing data comprising biometric parameters.

40. A system for transmitting energy to and communicating with an implantable medical device, the system comprising a transmission module that establishes a data transfer link with the implantable medical device, the system further comprising at least one energizable coil and adapted to automatically establish and control an inductive transfer link with the implantable medical device comprising at least one energizable coil, wherein the transmission module automatically initiates, without requiring user intervention, an inductive transfer of energy to the medical device to power the implantable medical device, the automatic initiation based at least in part on the medical device coming within range of the transmission module, wherein the inductive link powers at least one of: (1) intracorporeal ultrasound transmitters and receivers for data communication between multiple implantable devices, or (2) an RF transmitter and receiver.

41. The system of claim 40, wherein the link is a bi-directional data transfer link that is adapted to upload and download data.

42. The system of claim 40, wherein the transmission module establishes a data transfer link with a plurality of medical devices.

43. The system of claim 40, wherein the transmission module establishes a data transfer link with a centralized external patient management system.

44. The system of claim 40, wherein the inductive link modulates the data link.

45. The system of claim 40, wherein the inductive link powers the data link.

46. The system of claim 40, wherein the inductive link powers intracorporeal ultrasound transmitters and receivers for data communication between multiple implantable devices.

47. The system of claim 40, wherein the inductive link powers a RF transmitter and receiver.

48. The system of claim 40, wherein the RF transmitter and receiver comprises a Bluetooth® RF transmitter and receiver.

49. The system of claim 40, wherein the transmission module comprises a RF transmitter and receiver.

50. The system of claim 40, wherein the implantable medical device comprises a RF transmitter and receiver.

51. The system of claim 40, wherein the transmission module and the implantable medical device comprises an RF transmitter and receiver.

* * * * *

UNITED STATES PATENT AND TRADEMARK OFFICE
CERTIFICATE OF CORRECTION

PATENT NO. : 7,471,986 B2
APPLICATION NO. : 10/783285
DATED : December 30, 2008
INVENTOR(S) : Hatlestad

Page 1 of 1

It is certified that error appears in the above-identified patent and that said Letters Patent is hereby corrected as shown below:

In column 10, line 52, in Claim 51, delete "comprises" and insert -- comprise --, therefor.

Signed and Sealed this

Sixth Day of October, 2009

David J. Kappos
*Director of the United States Patent and Trademark Office*